United States Patent
Sun

(10) Patent No.: US 10,314,861 B2
(45) Date of Patent: *Jun. 11, 2019

(54) FLOWABLE TISSUE MATRICES

(71) Applicant: LifeCell Corporation, Branchburg, NJ (US)

(72) Inventor: Wenquan Sun, Warrington, PA (US)

(73) Assignee: LifeCell Corporation, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/684,402

(22) Filed: Aug. 23, 2017

(65) Prior Publication Data

US 2017/0348353 A1    Dec. 7, 2017

Related U.S. Application Data

(63) Continuation of application No. 13/868,588, filed on Apr. 23, 2013, now Pat. No. 9,782,436.

(60) Provisional application No. 61/637,419, filed on Apr. 24, 2012.

(51) Int. Cl.
| | |
|---|---|
| A61K 35/12 | (2015.01) |
| A61L 27/36 | (2006.01) |
| A61L 27/22 | (2006.01) |
| A61L 27/38 | (2006.01) |
| A61L 27/48 | (2006.01) |
| A61L 27/52 | (2006.01) |
| A61L 27/54 | (2006.01) |

(52) U.S. Cl.
CPC ............ *A61K 35/12* (2013.01); *A61L 27/222* (2013.01); *A61L 27/3683* (2013.01); *A61L 27/3834* (2013.01); *A61L 27/48* (2013.01); *A61L 27/52* (2013.01); *A61L 27/54* (2013.01); *A61L 2300/258* (2013.01); *A61L 2300/402* (2013.01); *A61L 2300/41* (2013.01); *A61L 2300/414* (2013.01); *A61L 2300/426* (2013.01); *A61L 2300/43* (2013.01); *A61L 2300/64* (2013.01); *A61L 2400/06* (2013.01); *A61L 2430/34* (2013.01); *A61L 2430/40* (2013.01)

(58) Field of Classification Search
CPC ...... C08L 89/06; A61L 27/52; A61L 27/3834; A61L 2400/06; A61L 27/222; A61K 2800/91; A61K 8/65; A61K 35/12; A61K 9/0019

See application file for complete search history.

(56) References Cited

U.S. PATENT DOCUMENTS

| | | |
|---|---|---|
| 4,582,640 A | 4/1986 | Smestad et al. |
| 4,902,508 A | 2/1990 | Badylak et al. |
| 4,969,912 A | 11/1990 | Kelman et al. |
| 5,104,957 A | 4/1992 | Kelman et al. |
| 5,131,850 A | 7/1992 | Brockbank |
| 5,160,313 A | 11/1992 | Carpenter et al. |
| 5,231,169 A | 7/1993 | Constantz et al. |
| 5,254,133 A | 10/1993 | Seid |
| 5,275,826 A | 1/1994 | Badylak et al. |
| 5,284,655 A | 2/1994 | Bogdansky et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,489,304 A | 2/1996 | Orgill et al. |
| 5,613,982 A | 3/1997 | Goldstein |
| 5,632,778 A | 5/1997 | Goldstein |
| 5,641,518 A | 6/1997 | Badylak et al. |
| 5,728,752 A | 3/1998 | Scopelianos et al. |
| 5,739,176 A | 4/1998 | Dunn et al. |
| 5,834,232 A | 11/1998 | Bishop et al. |
| 6,027,743 A | 2/2000 | Khouri et al. |
| 6,096,347 A | 8/2000 | Geddes et al. |
| 6,179,872 B1 | 1/2001 | Bell et al. |
| 6,194,136 B1 | 2/2001 | Livesey et al. |
| 6,326,018 B1 | 12/2001 | Gertzman et al. |
| 6,371,992 B1 | 4/2002 | Tanagho et al. |
| 6,432,710 B1 | 8/2002 | Boss, Jr. et al. |
| 6,485,723 B1 | 11/2002 | Badylak et al. |
| 6,576,265 B1 | 6/2003 | Spievack |

(Continued)

FOREIGN PATENT DOCUMENTS

| | | |
|---|---|---|
| WO | 2000/016822 A1 | 3/2000 |
| WO | 2000/047114 A1 | 8/2000 |

(Continued)

OTHER PUBLICATIONS

Ahn et al., "The past, present, and future of xenotransplantation" Yonsei Med J., 45(6):1017-1024 (Dec. 31, 2004).

(Continued)

*Primary Examiner* — Lynn Y Fan

(74) *Attorney, Agent, or Firm* — McCarter & English, LLP

(57) ABSTRACT

Disclosed herein are flowable tissue matrix compositions comprising small pieces of partially or completely decellularized tissue suspended in a gelatinized tissue or gelatin gel comprising partially or completely decellularized tissue or synthetic gelatin. The flowable tissue matrix compositions can contain factors that promote or enhance native cell migration, proliferation, and/or revascularization after implantation into a subject. Also disclosed are methods of making and using the flowable tissue matrix compositions. The compositions can be implanted into a tissue in need of repair, regeneration, healing, treatment, and/or alteration, and can promote or enhance native cell migration, proliferation, and/or revascularization.

20 Claims, 3 Drawing Sheets

(56) References Cited

U.S. PATENT DOCUMENTS

| | | |
|---|---|---|
| 6,666,892 B2 | 12/2003 | Hiles et al. |
| 6,933,326 B1 | 8/2005 | Griffey et al. |
| 6,998,418 B1 | 2/2006 | Sung et al. |
| 7,153,518 B2 | 12/2006 | Wironen et al. |
| 7,358,284 B2 | 4/2008 | Griffey et al. |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,799,767 B2 | 9/2010 | Lamberti et al. |
| 7,838,021 B2 | 11/2010 | Lafont et al. |
| 8,067,149 B2 | 11/2011 | Livesey et al. |
| 8,324,449 B2 | 12/2012 | McQuillan et al. |
| 2002/0103542 A1 | 8/2002 | Bilbo |
| 2003/0035843 A1 | 2/2003 | Livesey et al. |
| 2003/0039678 A1 | 2/2003 | Stone et al. |
| 2003/0143207 A1 | 7/2003 | Livesey et al. |
| 2004/0037735 A1 | 2/2004 | DePaula et al. |
| 2004/0078077 A1 | 4/2004 | Binette et al. |
| 2005/0028228 A1 | 2/2005 | McQuillan et al. |
| 2005/0159822 A1 | 7/2005 | Griffey et al. |
| 2005/0260176 A1 | 11/2005 | Ayares et al. |
| 2006/0073592 A1 | 4/2006 | Sun et al. |
| 2006/0210960 A1 | 9/2006 | Livesey et al. |
| 2007/0004961 A1 | 1/2007 | Case et al. |
| 2007/0078522 A2 | 4/2007 | Griffey |
| 2007/0104759 A1 | 5/2007 | Dunn et al. |
| 2007/0248575 A1 | 10/2007 | Connor et al. |
| 2008/0027542 A1 | 1/2008 | McQuillan et al. |
| 2008/0027562 A1 | 1/2008 | Fujisato et al. |
| 2009/0035289 A1 | 2/2009 | Wagner et al. |
| 2009/0306790 A1 | 12/2009 | Sun |
| 2010/0021961 A1 | 1/2010 | Fujisato et al. |
| 2010/0040687 A1 | 2/2010 | Pedrozo et al. |
| 2010/0209408 A1 | 8/2010 | A. et al. |
| 2010/0272782 A1 | 10/2010 | Owens et al. |
| 2011/0020271 A1 | 1/2011 | Niklason et al. |
| 2012/0010728 A1 | 1/2012 | Sun et al. |
| 2012/0040013 A1 | 2/2012 | Owens et al. |
| 2012/0263763 A1 | 10/2012 | Sun et al. |
| 2013/0053960 A1 | 2/2013 | Park et al. |
| 2013/0121970 A1 | 5/2013 | Owens et al. |
| 2013/0158676 A1 | 6/2013 | Klayzlett et al. |
| 2013/0280801 A1 | 10/2013 | Sun |

FOREIGN PATENT DOCUMENTS

| | | |
|---|---|---|
| WO | 2003/017826 A2 | 3/2003 |
| WO | 2003/032735 A1 | 4/2003 |
| WO | 2005/009134 A1 | 2/2005 |
| WO | 2007/043513 A1 | 4/2007 |
| WO | 2007/134134 A2 | 11/2007 |
| WO | 2009/009620 A2 | 1/2009 |
| WO | 2010/019753 A2 | 2/2010 |
| WO | 2010/078353 A2 | 7/2010 |
| WO | 2012/142419 A1 | 10/2012 |
| WO | 2012/166784 A1 | 12/2012 |

OTHER PUBLICATIONS

Allman et al., "Xenogeneic Extracellular Matrix Grafts Elicit a TH2-Restricted Immune Response" Transplantation, 71(11):1631-1640 (Jun. 15, 2001).

Aycock et al., "Parastomal Hernia Repair With Acellular Dermal Matrix" J. Wound Ostomy Continence Nurs., 34(5):521-523 (2007).

Badylak et al., "Endothelial cell adherence to small intestinal submucosa: An acellular bioscaffold" Biomaterials, 20:2257-2263 (1999).

Badylak et al., "Extracellular Matrix as a Biological Scaffold Material: Structure and Function" Acta Biomaterialia, 5(1):1-13 (2009).

B-Bridge International, Inc., Type 1 Collagenase Assay Kit. Catalog # AK07. www.b-bridge.com. 4 pages (2009).

Beniker et al., "The use of acellular dermal matrix as a scaffold for periosteum replacement" Orthopedics, 26(5 Suppl):s591-s596 (May 2003).

Bruder et al., "The Effect of Implants Loaded with Autologous Mesenchymal Stem Cells on the Healing of Canine Segmental Bone Defects" J. Bone Joint Surg., 80:985-986 (1998).

Buma et al., "Tissue engineering of the meniscus" Biomaterials, 25(9):1523-1532 (2004).

Chaplin et al., "Use of an Acellular Dermal Allograft for Dural Replacement: An Experimental Study" Neurosurgery, 45(2):320-327 (Aug. 1999).

Chen et al. "Acellular Collagen Matrix as a Possible 'Off the Shelf' Biomaterial for Urethral Repair" Urology, 54(3):407-410 (1999).

Collins et al., "Cardiac xenografts between primate species provide evidence for the importance of the ?-galactosyl determinant in hyperacute rejection" J. Immunol., 154:5500-5510 (1995).

Costantino et al., "Human Dural Replacement With Acellular Dermis: Clinical Results and a Review of the Literature" Head & Neck, 22:765-771 (Dec. 2000).

Dobrin et al., "Elastase, collagenase, and the biaxial elastic properties of dog carotid artery" Am. J. Physiol. Heart Circ. Physiol., 247:H124-H131 (1984).

Edel, "The use of a connective tissue graft for closure over an immediate implant covered with occlusive membrane" Clin. Oral Implants Res., 6:60-65 (1995) (Abstract).

Fowler et al., "Ridge Preservation Utilizing an Acellular Dermal Allograft and Demineralized Freeze-Dried Bone Allograft: Part II. Immediate Endosseous Impact Placement" J. Periodontol., 71:1360-1364 (2000).

Fowler et al., "Root Coverage with an Acellular Dermal Allograft: A Three-Month Case Report" J. Contemp. Dental Pract., 1(3):1-8 (2000).

Galili et al., "Man, Apes, and Old World Monkeys Differ from Other Mammals in the Expression of ?-Galactosyl Epitopes on Nucleated Cells" J. Biol. Chem., 263(33):17755-17762 (1988).

Galili et al., "Interaction Between Human Natural Anti-?-Galactosyl Immunoglobulin G and Bacteria of the Human Flora" Infect. Immun., 56(7):1730-1737 (1988).

Galili et al., "Interaction of the Natural Anti-Gal Antibody with ?-Galactosyl Epitopes: a Major Obstacle for Xenotransplantation in Humans" Immunology Today, 14(10):480-482 (1993).

Gamba et al. "Experimental abdominal wall defect repaired with acellular matrix" Pediatr. Surg. Int., 18:327-331 (2002).

Gebhart et al., "A radiographical and biomechanical study of demineralized bone matrix implanted into a bone defect of rat femurs with and without bone marrow" Acta Orthop. Belg., 57(2):130-143 (1991) (Abstract).

Hammond et al., "Parastomal Hernia Prevention Using a Novel Collagen Implant: A Randomised Controlled Phase 1 Study" Hernia, 12:475-481 (2008).

Kish et al., "Acellular Dermal Matrix (AlloDerm): New Material in the Repair of Stoma Site Hernias" The American Surgeon, 71:1047-1050 (Dec. 2005).

Kridel et al., "Septal Perforation Repair with Acellular Human Dermal Allograft" Arch. Otolaryngol. Head Neck Surg., 124:73-78 (Jan. 1998).

Laidlaw et al., "Tympanic Membrane Repair With a Dermal Allograft" Laryngoscope, 111:702-707 (Apr. 2001).

Lee et al., "In vitro evaluation of a poly(lactide-co-glycolide)-collagen composite scaffold for bone regeneration" Biomaterials, 27:3466-3472 (2006).

Liang et al., Effects of crosslinking degree of an acellular biological tissue on its tissue regeneration pattern. Biomaterials. Aug. 2004;25(17):3541-52.

Lu et al., "Novel Porous Aortic Elastin and Collagen Scaffolds for Tissue Engineering" Biomaterials, 25(22):5227-5237 (2004).

Simon et al., "Early failure of the tissue engineered porcine heart valve SYNERGRAFT™ in pediatric patients" Eur. J. Cardiothorac. Surg., 23(6):1002-1006 (2003).

(56) References Cited

OTHER PUBLICATIONS

Zheng et al. "Porcine small intestine submucosa (SIS) is not an acellular collagenous matrix and contains porcine DNA: Possible implications in human implantation" J. Biomed. Mater Res. B: Appl. Biomater., 73(1):61-67 (2005).
Office Action dated Jan. 29, 2014 issued in U.S. Appl. No. 13/717,828, filed Dec. 18, 2012.

FLOWABLE TISSUE MATRICES

REFERENCE TO RELATED APPLICATIONS

This application is a continuation of U.S. patent application Ser. No. 13/868,588, filed Apr. 23, 2013, which claims priority to U.S. Provisional Application No. 61/637,419, filed Apr. 24, 2012, which is incorporated herein by reference in its entirety.

The present disclosure relates generally to methods of making and using compositions comprising flowable tissue matrices.

Acellular tissue matrices of both animal and human origin are used for soft tissue repair and regeneration. Currently, acellular tissue is often used in sheet form. Sheets of acellular tissue, however, present practical limitations, such as limits on the ability to mold the tissue into a desired shape to match the structure of an anatomical implant site. Alternative structures, such as particulate acellular tissue, are limited by their speed of resorption, degradation, or migration away from the site of implantation. In addition, particulate acellular tissue is often stored freeze-dried, thereby requiring time-consuming rehydration prior to use in the surgical setting.

Accordingly, disclosed herein are flowable tissue matrix compositions, comprising small pieces of partially or completely decellularized tissue suspended in a gelatinized tissue or gelatin gel. In some embodiments, the volume of gelatinized tissue or gelatin gel is minimized in order to reduce the amount of denatured collagen present in the compositions and/or to avoid disrupting the migration, proliferation, or revascularization of an implanted composition. In some embodiments, the small pieces of partially or completely decellularized tissue in a flowable tissue matrix composition are selected such that a majority of the pieces minimize their surface area to volume ratio, for example by producing pieces having a ratio of less than about 6 $mm^2/mm^3$. In some embodiments, the small pieces of partially or completely decellularized tissue in a flowable tissue matrix composition are selected such that a majority of the pieces have a surface area to volume ratio less than about 6.0, 5.5, 5.0, or 4.5 $mm^2/mm^3$ (or any value in between) and greater than about 1.0, 1.1, 1.2, 1.3, 1.4, 1.5, 1.6, 1.7, 1.8, 1.9, or 2.0 $mm^2/mm^3$ (or any value in between). As used herein, a "majority" indicates at least about 50% of the small pieces (e.g., at least about 50, 55, 60, 65, 70 75, 80, 85, 90, 85, 99, or 99.9%) (or any percentage in between).

In some embodiments, the small pieces of decellularized tissue are selected or processed to have dimensions large enough to avoid rapid degradation, but small enough to exhibit improved flowable or malleable characteristics and to allow for the use of a low or reduced amount of gelatin or gelatin gel. For example, suitable pieces of decellularized tissue can have dimensions (i.e., a length, width, and/or height) ranging from about 1.0 mm to about 5.0 mm (e.g., dimensions of about 1.0, 1.5, 2.0, 2.5, 3.0, 3.5, 4.0, 4.5, or 5.0 mm) (or any value in between). For example, the dimensions can range between about 1.0 mm and 5.0 mm, or between about 1.5 mm and 4.5 mm, or between about 2.0 mm and 4.0 mm. In certain embodiments, flowable tissue matrix compositions have increased resistance to degradation, migration, or resorption, as compared to homogenized acellular tissue, while also retaining the ability to flow into and mold to the shape of an implant site. In some embodiments, the small pieces of partially or completely decellularized tissue have a length, a width, and a height, and wherein each of the length, width, and height have dimensions ranging from about 1.0 mm to about 5.0 mm.

In various embodiments, the gelatinized tissue or gelatin gel comprises a synthetic material or a homogenized acellular or partially decellularized tissue in an aqueous solution at a concentration of about 0.1-10.0% w/v. In certain embodiments, the gelatin gel is crosslinked.

In various embodiments, the small pieces of partially or completely decellularized tissue, the gelatinized tissue and/or the gelatin gel are derived from at least one of human, nonhuman primate, pig, cow, horse, goat, sheep, dog, cat, rabbit, guinea pig, gerbil, hamster, rat, and mouse tissue, and/or at least one of bone, skin, dermis, intestine, vascular, urinary bladder, tendon, ligament, muscle, fascia, neurologic tissue, vessel, liver, heart, lung, kidney, and cartilage tissue. In some embodiments, the compositions lack substantially all alpha-galactose moieties. In various embodiments, a flowable tissue matrix composition has a reduced bioburden or substantially lacks all bioburden.

In various embodiments, flowable tissue matrix compositions comprise one or more viable cells, such as stem cells, and/or at least one additional factor, such as an anti-inflammatory agent, an analgesic, a cell growth factor, an angiogenic factor, a differentiation factor, a cytokine, a hormone, or a chemokine.

In some embodiments, a kit is provided, comprising a flowable tissue matrix composition as disclosed herein and instructions for using the kit. In certain embodiments, the kit is packaged under aseptic or sterilize conditions. In some embodiments, the kit comprises a syringe or other delivery device preloaded with a flowable tissue matrix composition in aqueous form and ready for delivery to a surgical site on a patient.

In various embodiments, a method is disclosed for making a flowable tissue matrix composition, comprising selecting a tissue containing an extracellular matrix; partially or completely decellularizing the tissue; processing the decellularized tissue to produce small pieces of the tissue (e.g., pieces having dimensions ranging from about 1.0 mm to about 5.0 mm in length); gelatinizing a partially or completely decellularized tissue; optionally heating and cooling the gelatinized tissue to produce a gelatin gel; and combining the small pieces of decellularized tissue with the gelatinized tissue or gelatin gel. In some embodiments, processing the partially or completely decellularized tissue into small pieces comprises cutting the partially or completely decellularized tissue into pieces having a length, a width, and a height, and wherein each dimension is between about 1.0 mm and 5.0 mm. In certain embodiments, gelatinizing the partially or completely decellularized tissue comprises suspending the partially or completely decellularized tissue in a solution containing one or more Lewis bases (such as sodium carbonate, sodium citrate, or sodium acetate) and homogenizing the tissue. In some embodiments, producing a gelatin gel comprises placing a gelatinized tissue in a hydrating solution, heating the tissue, and then allowing the tissue to cool. In some embodiments, a gelatin gel is selected from biocompatible synthetic materials that have a viscous consistency. In certain embodiments, the gelatin gel is cross-linked by contacting the tissue with a cross-linking agent, such as pentagalloyl glucose (PGG), glutaraldehyde, or genipin.

In various embodiments, the small pieces of decellularized tissue are combined with a minimal volume of gelatinized tissue or gelatin gel in order to minimize the percentage of gelatinized tissue or gelatin gel in the composition, as compared to the percentage of small pieces of decellularized tissue in the overall composition (measured on a mass/volume or volume/volume basis). For example, small pieces of decellularized tissue (e.g., pieces having dimensions between about 1.0 mm and about 5.0 mm and/or a surface area to volume ratio between about 1 mm$^2$/mm$^3$ and 6 mm$^2$/mm$^3$) can be held together in a structurally stable composition when up to about 95% (or 90%, 80%, 70%, or 60%, or any percentage in between) of the composition (w/v or v/v) comprises small pieces of tissue, with the remaining approximately 5% (or 10%, 20%, 30%, or 40%, or any percentage in between) comprising gelatin or gelatin gel. In contrast, larger pieces of decellularized tissue may require additional gelatin or gelatin gel in order to adhere (e.g., to "glue") the pieces together into a structurally stable composition that will not migrate (e.g., break apart) into separate and disparate pieces of decellularized tissue after implantation (e.g., potentially needing up to 50% or more gelatin or gelatin gel).

In some embodiments, the dimensions of the small pieces of decellularized tissue are selected such that a majority of the pieces minimize their surface area to volume ratio, for example, by having a ratio of less than about 6 mm$^2$/mm$^3$. In some embodiments, the small pieces of partially or completely decellularized tissue in a flowable tissue matrix composition are selected such that a majority of the pieces have a surface area to volume ratio of less than about 6.0, 5.5, 5.0, or 4.5 mm$^2$/mm$^3$ (or any value in between) and greater than about 1.0, 1.1, 1.2, 1.3, 1.4, 1.5, 1.6, 1.7, 1.8, 1.9, or 2.0 mm$^2$/mm$^3$ (or any value in between). As used herein, a "majority" indicates at least about 50% of the small pieces (e.g., at least about 50, 55, 60, 65, 70 75, 80, 85, 90, 85, 99, or 99.9%) (or any percentage in between).

In certain embodiments, the flowable tissue matrix composition is irradiated to reduce bioburden, for example using 15-25 kGy E-beam irradiation.

Also disclosed herein, according to certain embodiments, are methods of treatment, comprising implanting a flowable tissue matrix composition, as disclosed herein, into a tissue in need of repair, regeneration, healing, treatment, or alteration. In various embodiments, an implanted flowable tissue matrix composition provides a structural scaffold into which native cells from surrounding tissue can migrate and proliferate. In some embodiments, the implanted flowable tissue matrix composition has increased resistance to degradation, migration and/or resorption, as compared to homogenized acellular tissue, while also retaining the ability to flow into and mold to the shape of an implant site. In some embodiments, the implanted flowable tissue matrix composition reduces bleeding at an implant site (e.g., via the gelatin or gelatin gel more fully filling an implant site and blocking a source of bleeding).

In various embodiments, a flowable tissue matrix composition can be implanted for cosmetic purposes, for example, in combination with a breast implant. In other embodiments, a flowable tissue matrix composition can be implanted following the removal of native tissue, such as a tumor. In some embodiments, implanting a flowable tissue matrix composition preserves the look or feel of native tissue after it has been removed, as compared to the look or feel in the absence of an implanted flowable tissue matrix composition. In other embodiments, a flowable tissue matrix composition can be implanted following surgical separation of native tissues or in a wound or other void space that occurs through injury or disease. In some embodiments, implanting the flowable tissue matrix composition leads to faster healing, as compared to healing in the absence of an implanted flowable tissue matrix composition.

DESCRIPTION OF THE DRAWINGS

FIG. 6A shows the increase in free amine concentration (in mM, normalized to a 1000 mg sample weight) for acellular porcine dermal cubes of different sizes (measured in mm) after 18 hours in a collagenase solution. FIG. 6B shows the percentage of tissue remaining after incubating acellular porcine dermal cubes of different sizes (measured in mm) for 48 hours in a collagenase solution.

DESCRIPTION OF CERTAIN EXEMPLARY EMBODIMENTS

Figure 1:
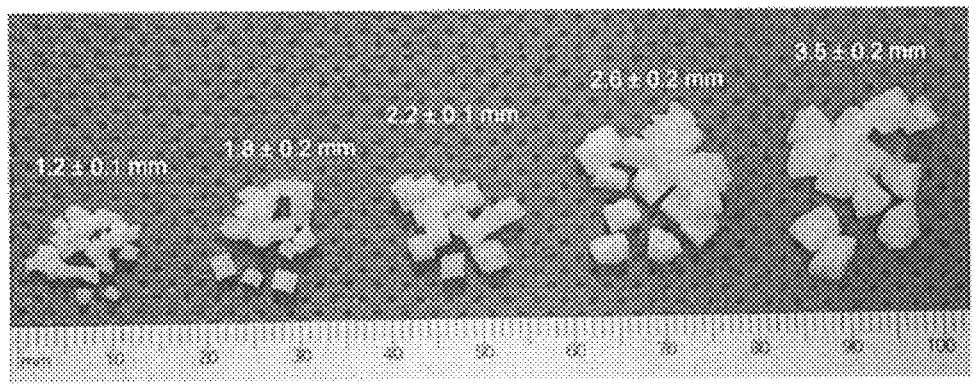
FIG. 1 shows cubes of acellular porcine dermis of different dimensions.

Reference will now be made in detail to certain exemplary embodiments according to the present disclosure, certain examples of which are illustrated in the accompanying drawings.

Disclosed herein are flowable tissue matrix compositions, comprising small pieces of partially or completely decellularized tissue suspended in a minimal volume of gel, comprising gelatinized tissue that has been partially or completely decellularized, or comprising a synthetic gelatin material. This two component system provides increased stability and resistance against migration and proteolytic degradation, while also retaining the flowable and moldable properties associated with particulate acellular tissue. The flowable tissue matrices can be stored in hydrated form for extended periods of time and can be surgically implanted as bulk soft tissue filler. For example, flowable tissue matrices can be implanted following the surgical removal of bulk soft tissue, or as an implant for cosmetic purposes, or to fill a wound resulting from disease, trauma or surgery.

In some embodiments, a flowable tissue matrix composition is prepared by first preparing small pieces of acellular tissue by cutting or otherwise processing partially or completely decellularized tissue into small pieces. In certain embodiments, acellular or partially decellularized tissue is gelatinized by incubating acellular or partially decellularized tissue in a solution containing a Lewis base such as sodium carbonate, sodium citrate, and/or sodium acetate. In some embodiments, a gelatin gel is derived from gelatinized tissue by heating the tissue, for example to 40-60° C., and then cooling to room temperature. In certain embodiments, a gelatin gel can comprise biocompatible synthetic material having a viscous consistency. In some embodiments, the gelatin gel can be cross-linked. In various embodiments, cubes or other small pieces of acellular tissue are suspended in the gelatinized tissue or gelatin gel. In certain embodiments, the amount of gelatinized tissue or gelatin gel is minimized, e.g., in order to minimize the volume of disrupted collagen in the composition. In some embodiments, the surface area to volume ratio of the small pieces of decellurized tissue is minimized (e.g., by reducing below a ratio of about 6 $mm^2/mm^3$), thereby increasing the composition's resistance to degradation, migration and/or resorption. In some embodiments, the use of gelatin or gelatin gel also allows the composition to retain the flowable and moldable characteristics of particulate tissue.

The flowable tissue matrix compositions disclosed herein can be used, in various embodiments, to repair, regenerate, heal, treat, and/or alter a tissue in need thereof. For example, a flowable tissue matrix composition can be implanted to provide a biological or synthetic scaffold into which native cells from tissue surrounding the compositions can migrate and proliferate, and which will resist degradation or migration away from the site of implantation. The flowable tissue matrices can be stored in hydrated form for extended periods of time and can be surgically implanted as a soft tissue filler without the need to rehydrate the composition prior to use, thereby avoiding the risk of over-rehydrating and/or the delay associated with rehydration procedures. For example, the flowable tissue matrices can be implanted following the surgical removal of bulk soft tissue, as an implant for cosmetic purposes, or to fill a wound or separated tissue resulting from disease, trauma or surgery. In addition, in certain embodiments, the gelatinized tissue or gelatin gel in a flowable tissue matrix composition can be used to help stop bleeding at an implant site. In some embodiments the flowable tissue matrix compositions can be used to deliver enzymes, signaling molecules, or other factors to the tissue in need of repair, regeneration, or treatment, thereby promoting or enhancing the repopulation and/or revascularization of the implant with native cells from surrounding tissue.

The materials and methods provided herein can be used to make a biocompatible, implantable composition. As used herein, a "biocompatible" composition is one that has the ability to support the migration and proliferation of native cells from surrounding tissue into the composition following implantation. Biocompatible compositions support the native cellular activity necessary for tissue regeneration, repair, healing, or treatment and do not elicit a substantial immune response that prevents such cellular activity. As used herein, a "substantial immune response" is one that prevents partial or complete tissue regeneration, repair, healing, or treatment.

As used herein, the terms "native cells" and "native tissue" mean the cells or tissue present in the recipient organ or tissue prior to implantation of a flowable tissue matrix composition, or the cells or tissue produced by the host animal after implantation.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described here will be understood to include the endpoints and all values between the endpoints.

Flowable Tissue Matrices

In various embodiments, a flowable tissue matrix composition comprises human or animal tissue that has been at least partially decellularized. The tissue can be acellular, partially decellularized, and/or decellularized tissue that has been repopulated with exogenous cells, so long as the tissue retains at least some of the extracellular matrix found in the tissue prior to decellularizing.

In certain embodiments, a flowable tissue matrix composition can be derived from any human or animal tissue that is suitable for partial or complete decellularization and subsequent implantation. Exemplary tissues include, but are not limited to, bone, skin, dermis, intestine, urinary bladder, tendon, ligament, muscle, fascia, neurologic tissue, vascular tissue, vessel, liver, heart, lung, kidney, cartilage, and/or any other suitable tissue. In certain embodiments, a flowable tissue matrix composition can include a mammalian soft tissue. For example, in certain embodiments, a flowable tissue matrix composition can include partially or completely decellularized mammalian dermis. As another example, a flowable tissue matrix composition can comprise partially or completely decellularized mammalian small intestine submucosa, or partially or completely decellularized mammalian lung or liver tissue. A flowable tissue matrix composition can comprise tissue from one or more (e.g, 1, 2, 3, 4, 5, or more) different tissue sources. In certain embodiments, the decellularized tissue can come from human or non-human sources. Exemplary, suitable non-human tissue sources include, but are not limited to, pigs, sheep, goats, cows, rabbits, monkeys, and/or other non-human mammals. A flowable tissue matrix composition can comprise tissue from one or more (e.g, 1, 2, 3, 4, 5, or more) different animal sources.

In some embodiments, a flowable tissue matrix composition can be formed from ALLODERM® or STRATTICE™ (LIFECELL Corporation, Branchburg, N.J.), which are human and porcine acellular dermal matrices respectively. Alternatively, any other suitable acellular tissue matrices can be used. For example, a number of biological scaffold materials are described by Badylak et al., and the methods of the present disclosure can be used to produce a stable three-dimensional acellular tissue matrix using any of those materials, or any other similar materials. Badylak et al., "Extracellular Matrix as a Biological Scaffold Material: Structure and Function," *Acta Biomaterialia* (2008), doi: 10.1016/j.actbio.2008.09.013, hereby incorporated by reference in its entirety.

In various embodiments, the extracellular scaffold within an acellular or partially decellularized tissue matrix may consist of collagen, elastin, or other fibers, as well as proteoglycans, polysaccharides and growth factors. The tissue matrix may retain some or all the extracellular matrix components that are found naturally in a tissue prior to decellularization, or various undesirable components may be removed by chemical, enzymatic or genetic means. In general, the acellular matrix provides a structural network of fibers, proteoglycans, polysaccharides, and growth factors on which native tissue and vasculature can migrate, grow, and proliferate. The exact structural components of the extracellular matrix will depend on the tissue selected and the processes used to prepare the acellular or partially decellularized tissue.

In certain embodiments, a flowable tissue matrix composition lacks certain undesirable antigens. For example, certain animal tissues contain alpha-galactose (α-gal) epitopes that are known to elicit reactions in humans. Therefore, flowable tissue matrix compositions derived from various animal tissues can be produced or processed to lack certain antigens, such as α-gal. In some embodiments, flowable tissue matrix compositions lack substantially all α-gal moieties. Elimination of the α-gal epitopes may diminish the immune response against the composition. U. Galili et al., *J. Biol. Chem.* 263: 17755 (1988). Since non-primate mammals (e.g., pigs) produce α-gal epitopes, xenotransplantation of acellular tissue matrix material from these mammals into primates may result, in some instances, in rejection because of primate anti-gal binding to the α-gal epitopes on the acellular tissue matrix. The binding results in the destruction of the acellular tissue by complement fixation and by antibody-dependent cell cytotoxicity. U. Galili et al., *Immunology Today* 14: 480 (1993); M. Sandrin et al., *Proc. Natl. Acad. Sci.* USA 90: 11391 (1993); H. Good et al., *Transplant. Proc.* 24: 559 (1992); B. H. Collins et al., *J. Immunol.* 154: 5500 (1995).

As described in detail below, in various embodiments, flowable tissue matrix compositions can be processed to remove antigens such as α-gal, e.g., by chemical or enzymatic treatment. Alternatively, in some embodiments, flowable tissue matrix compositions can be produced from animals that have been genetically modified to lack these epitopes.

Flowable tissue matrix compositions can be selected to provide a variety of different biological and mechanical properties. For example, a flowable tissue matrix composition can be selected in order to provide a scaffold in which native cells from tissue surrounding an implanted composition can migrate and proliferate, thereby enhancing the speed or overall level of repair, regeneration, healing, and/or treatment of native tissue. For example, an acellular tissue matrix, when implanted on or into fascia, may be selected to allow for regeneration of the fascia without excessive fibrosis or scar formation.

In certain embodiments, flowable tissue matrix compositions comprising human or animal tissue are completely or substantially free of all cells normally present in the tissue from which the composition is derived. As used herein, "substantially free of all cells" means that a flowable tissue matrix composition contains less than 20%, 10%, 5%, 1%, 0.1%, 0.01%, 0.001%, or 0.0001% (or any percentage in between) of the cells that normally grow within the acellular matrix of the tissue prior to decellularization.

In some embodiments, flowable tissue matrix compositions can include extracellular scaffolds that have been repopulated with viable cells. Various cell types can be used for repopulation, including stem cells such as embryonic stem cells, adult stem cells (e.g. mesenchymal stem cells), and/or neuronal cells. Any other viable cells can also be used. In some embodiments, the cells are mammalian cells. Such cells can promote native tissue migration, proliferation, and/or vascularization. In various embodiments, the viable cells are applied to the acellular tissue matrix before or after implantation of a flowable tissue matrix composition.

In certain embodiments, flowable tissue matrix compositions comprise one or more additional agents. In some embodiments, the additional agent(s) can comprise an anti-inflammatory agent, an analgesic, or any other desired therapeutic or beneficial agent. In certain embodiments, the additional agent(s) can comprise, e.g., at least one added growth or signaling factor (e.g., a cell growth factor, an angiogenic factor, a differentiation factor, a cytokine, a hormone, and/or a chemokine). These additional agents can promote native tissue migration, proliferation, and/or vascularization. In some embodiments, the growth or signaling factor is encoded by a nucleic acid sequence contained within an expression vector. Preferably, the expression vector is in one or more of the viable cells that can be added, optionally, to a flowable tissue matrix composition. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, initiation and termination codons, etc.) to ensure at least minimal expression of the desired protein by the cell.

In various embodiments, flowable tissue matrix compositions comprise small pieces of partially or completely decellularized tissue suspended in decellularized tissue that has been gelatinized or processed into a gelatinzed gel. In some embodiments, the small pieces of decellularized tissue can have three dimensions (a length, a width, and a height) that range in size from about 1.0 mm to about 5.0 mm (e.g., about 1.0 mm, 1.5 mm, 2.0 mm, 2.5 mm, 3.0 mm, 3.5 mm, 4.0 mm, 4.5 mm, or 5.0 mm, or any size in between). In some embodiments, the pieces can have regular shapes (e.g., spheres, cubes, rhomboids) or irregular shapes, as long as they generally have dimensions ranging from about 1.0 mm-5.0 mm.

In various embodiments, flowable tissue matrix compositions comprise small pieces of partially or completely decellularized tissue that are suspended in a gelatin comprising homogenized acellular or partially decellularized tissue. In certain embodiments, the gelatin comprises homogenized acellular or partially decellularized tissue suspended in an aqueous solution, wherein the homogenized tissue is present at a concentration of about 0.1-10.0% w/v (dry tissue mass/total solution volume), e.g., about 0.1, 0.2, 0.3, 0.4, 0.5, 1.0, 1.5, 2.0, 3.0, 4.0, 5.0, 6.0, 7.0, 8.0, 9.0, or 10.0% w/v (or any percentage in between). In some embodiments, the aqueous solution can include a Lewis base (such as sodium carbonate, sodium citrate, and/or sodium acetate), which is used to expand and/or dissolve the acellular or partially decellularized tissue within the gelatin, and a Lewis acid (such as HCl), which is used to neutralize the Lewis base prior to combining the gelatin with the small pieces of partially or completely decellularized tissue.

In various embodiments, the small pieces of partially or completely decellularized tissue are suspended in a gelatin gel comprising gelatinized tissue that has been placed in a hydrating solution such as distilled water, phosphate buffered saline (PBS), or any other biocompatible saline solution, heated, and then allowed to cool. In certain embodiments, the decellularized tissue in the gelatin gel is present at about 0.1-10.0% w/v (dry tissue mass/total solution volume), e.g., about 0.1, 0.2, 0.3, 0.4, 0.5, 0.6, 0.7, 0.8, 0.9, 1.0, 1.5, 2.0, 3.0, 4.0, 5.0, 6.0, 7.0, 8.0, 9.0, or 10.0% w/v (or any percentage in between).

In certain embodiments, a gelatin gel comprises a biocompatible synthetic gel material having a viscous consistency, such as a hydrogel, starch gel, or other polysaccharide gel. In some embodiments, a gelatin gel comprises one or more gelatinized tissues and one or more synthetic gel materials.

In various embodiments, the gelatin gel comprises homogenized acellular or partially decellularized tissue or a synthetic material that has been cross-linked. In certain embodiments, the cross-linked, decellularized tissue or synthetic material in the gelatin gel is present at 0.1-10.0% w/v (dry mass/total solution volume), e.g., about 0.1, 0.2, 0.3, 0.4, 0.5, 0.6, 0.7, 0.8, 0.9, 1.0, 1.5, 2.0, 3.0, 4.0, 5.0, 6.0, 7.0, 8.0, 9.0, or 10.0% w/v (or any percentage in between).

In various embodiments, implanted flowable tissue matrix compositions have increased resistance to degradation and/or resorption following implantation into a host tissue, as compared to an implanted homogenized acellular tissue. In certain embodiments, the size of the pieces or fragments of acellular tissue within the flowable composition is a physical parameter affecting the rheological properties of the composition, as well as a parameter regulating the biological response upon implantation (for example, regulating the ability to resist degradation, migration, and/or resorption). In this regard, the surface area to volume ratio of the small pieces of decellularized tissue within a flowable tissue matrix composition can alter the kinetics of degradation and remodeling, with larger pieces generally being more resistant to degradation or migration. But, larger pieces are also often less flowable or malleable and additional gelatin or gelatin gel may be required in order to adhere the larger pieces in an intact composition. Accordingly, the use of pieces of decellularized tissue having optimized dimensions (e.g., in a range between about 1.0 mm and 5.0 mm) can enable the flowable composition to exhibit the malleability of a homogenized tissue, while avoiding rapid degradation and/or the need to use an increased amount of gelatin or gelatin gel.

Accordingly, in some embodiments, the surface area to volume ratio of each piece of decellurized tissue in a flowable tissue matrix composition is minimized (e.g., by selecting or producing pieces of tissue having a ratio below about 6 $mm^2/mm^3$), such that the overall composition containing these small pieces can retain its moldable rheological properties using a minimal amount of gelatin or gelatin gel while increasing the composition's resistance to resorption, migration, and/or degradation (e.g., collagenase degradation) following implantation.

In certain embodiments, flowable tissue matrix compositions comprise small pieces of partially or completely decellularized tissue suspended in a minimal volume of gelatinized tissue or gelatin gel. In certain embodiments, a "minimal volume" of gelatinized tissue or gelatin gel is the amount that is sufficient to fill the space between the small pieces of decellularized tissue and/or which results in a flowable composition that retains structural integrity following implantation (e.g., where the small pieces of decellularized tissue remain clustered in close proximity following implantation) and/or results in a flowable composition that resists degradation or migration following implantation. For example, a flowable tissue matrix composition can comprise about 10-40 g (e.g., about 10, 11, 12, 13, 14, 15, 16, 17, 18, 19, 20, 25, 26, 27, 28, 29, 30, 31, 32, 33, 34, 35, or 40 g, or any amount in between) of decellularized tissue pieces having dimensions of about 1.0-5.0 mm (e.g., about 1.0, 1.5, 2.0, 2.5, 3.0, 3.5, 4.0, 4.5, or 5.0 mm, or any value in between) for every 1-15 ml of gelatinized tissue or gelatin gel (e.g., about 1, 2, 3, 4, 5, 6, 7, 8, 9, 10, 11, 12, 13, 14, or 15 ml, or any volume in between). For example, a flowable tissue matrix composition can comprise about 30 g of decellularized tissue having dimensions of about 3.5 mm suspended in about 9 ml of about 1.0% gelatin gel. In another example, a flowable tissue matrix composition can comprise about 15 g of decellularized tissue having dimensions of about 2.2 mm suspended in about 5 ml of about 1.0% gelatin gel. In some embodiments, the surface area to volume ratio of each small piece of decellularized tissue is less than about 6 $mm^2/mm^3$ (e.g., less than about 6.0, 5.0, 4.0, 3.0, 2.0, 1.0, 0.5, 0.4, or 0.3 $mm^2/mm^3$) (or any value in between). In some embodiments, the small pieces of partially or completely decellularized tissue in a flowable tissue matrix composition are selected such that a majority of the pieces have a surface area to volume ratio less than about 6.0, 5.5, 5.0, or 4.5 $mm^2/mm^3$ (or any value in between) and greater than about 1.0, 1.1, 1.2, 1.3, 1.4, 1.5, 1.6, 1.7, 1.8, 1.9, or 2.0 $mm^2/mm^3$ (or any value in between). As used herein, a "majority" indicates at least about 50% of the small pieces (e.g., at least about 50, 55, 60, 65, 70 75, 80, 85, 90, 85, 99, or 99.9%) (or any percentage in between).

Flowable tissue matrix compositions, as described above, may be packaged as frozen, freeze-dried, hydrated, and/or dehydrated products. In certain embodiments, the packaged flowable tissue matrix compositions are sterile. In certain embodiments, the flowable tissue matrix compositions are provided in a kit, comprising a packaged flowable tissue matrix composition and instructions for preparing and/or using the flowable tissue matrix composition. In some embodiments, the kit comprises a syringe or other device for delivering a flowable tissue matrix composition to a surgical implant site. In some embodiments, the flowable tissue matrix composition can be pre-loaded in hydrated form in the delivery device to allow for delivery to an implant site without first requiring rehydrating or other processing steps.

Methods of Making Flowable Tissue Matrices

Disclosed herein are methods of making flowable tissue matrices. In some embodiments, the method comprises selecting a tissue containing an extracellular matrix; partially or completely decellularizing the tissue; processing the decellularized tissue to produce small pieces; gelatinizing some of the decellularized tissue; and combining the pieces of decellularized tissue with the gelatinized tissue.

In some embodiments, a flowable tissue matrix can be prepared from any tissue that is suitable for decellularization and subsequent implantation. Exemplary tissues include, but are not limited to, bone, skin, dermis, intestine, urinary bladder, tendon, ligament, muscle, fascia, neurologic tissue, vascular tissue, vessel, liver, heart, lung, kidney, cartilage, and/or any other suitable tissue. In certain embodiments, the tissues can include a mammalian soft tissue. For example, in certain embodiments, the tissue can comprise mammalian dermis. In certain embodiments, the dermis can be separated from surrounding epidermis and/or other tissues, such as subcutaneous fat. In certain embodiments, the tissue can comprise mammalian small intestine submucosa. In certain embodiments, the tissue can include human and/or non-human sources. Exemplary, suitable non-human tissue sources include, but are not limited to, pigs, sheep, goats, cows, rabbits, monkeys, and/or other non-human mammals.

In some embodiments, a flowable tissue matrix is prepared by partially or completely decellularizing a donor tissue. Exemplary methods for decellularizing tissue are disclosed in U.S. Pat. No. 6,933,326 and U.S. Patent Application 2010/0272782, which are hereby incorporated by reference in their entirety. In some embodiments, the decellularized tissue provides a porous extracellular scaffold structure into which cells from surrounding native tissue can migrate and proliferate after implantation into a host site. In certain exemplary embodiments, the acellular tissue comprises ALLODERM® or STRATTICE™, which are acellular human dermal products and porcine dermal products, respectively, and are available from LifeCell Corporation (Branchburg, N.J.).

In various embodiments, the general steps involved in the production of an acellular or partially decellularized tissue matrix include providing tissue from a donor (e.g., a human cadaver or animal source) and removing cells under conditions that preserve the biological and structural functions of the extracellular matrix. In certain embodiments, the tissue can be washed to remove any residual cryoprotectants and/or other contaminants. Solutions used for washing can be any physiologically-compatible solution. Examples of suitable wash solutions include distilled water, phosphate buffered saline (PBS), or any other biocompatible saline solution.

In certain embodiments, the washed tissue can be chemically treated to stabilize the tissue so as to avoid biochemical and/or structural degradation before, during, or after cell removal. In various embodiments, the stabilizing solution arrests and prevents osmotic, hypoxic, autolytic, and/or proteolytic degradation; protects against microbial contamination; and/or reduces mechanical damage that can occur during decellularization of tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

In various embodiments, the tissue can be placed in a decellularization solution to remove viable and non-viable cells (e.g., epithelial cells, endothelial cells, smooth muscle cells, and fibroblasts, etc.) from the extracellular matrix without damaging the biological and/or structural integrity of the extracellular matrix. The decellularization solution may contain an appropriate buffer, salt, an antibiotic, one or more detergents (e.g., TRITON X-100™ sodium dodecyl sulfate, sodium deoxycholate, polyoxyethylene (20) sorbitan mono-oleate, etc.), one or more agents to prevent cross-linking, one or more protease inhibitors, and/or one or more enzymes. In some embodiments, the decellularization solution comprises 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of TRITON X-100™ and, optionally, 10 mM, 15 mM, 20 mM, 25 mM, 30 mM, 35 mM, 40 mM, 45 mM, or 50 mM EDTA (ethylenediaminetetraacetic acid) (or any concentration in between). In certain embodiments, the decellularization solution comprises 0.1%, 0.2%, 0.3%, 0.4%, 0.5%, 1.0%, 1.5%, 2.0%, 2.5%, 3.0%, 3.5%, 4.0%, 4.5%, or 5.0% (or any percentage in between) of sodium deoxycholate and, optionally, 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, or 20 mM HEPES buffer (4-(2-hydroxyethyl)-1-piperazineethanesulfonic acid) containing 10 mM, 15 mM, 20 mM, 25 mM, 30 mM, 35 mM, 40 mM, 45 mM, or 50 mM EDTA (or any concentrations in between). In some embodiments, the tissue is incubated in the decellularization solution at 20, 21, 22, 23, 24, 25, 30, 31, 32, 33, 34, 35, 36, 37, 38, 39, 40, 41, or 42 degrees Celsius (or any temperature in between), and optionally, gentle shaking is applied at 10, 20, 30, 40, 50, 60, 70, 80, 90, 100, 110, 120, 130, 140, or 150 rpm (or any rpm in between). The incubation can be for 1, 2, 3, 4, 5, 6, 7, 8, 9, 10, 11, 12, 15, 20, 24, 36, 48, or 96 hours (or any time in between). The length of time of exposure to the decellularization solution, or the concentration of detergent and/or other decellularizing agents can be adjusted in order to partially or more fully decellularize the tissue. In certain embodiments, additional detergents may be used to remove cells from the tissue sample. For example, in some embodiments, sodium deoxycholate and TRITON X-100™ are used to decellularize and separate other undesired tissue components from the extracellular tissue matrix.

In certain embodiments, the decellularized tissue can be placed in a solution containing calcium hydroxide. In some embodiments, the calcium hydroxide is at a concentration of about 0.05%-1.0% (w/v) calcium hydroxide (e.g., about 0.05, 0.1, 0.15, 0.2, 0.25, 0.3, 0.35, 0.4, 0.45, 0.5, 0.6, 0.7, 0.8, 0.9, or 1.0% w/v) (or any percentage in between). In some embodiments, the tissue is placed in the calcium hydroxide solution at about 20-40° C. (e.g., about 20, 21, 22, 23, 24, 25, 26, 27, 28, 29, 30, 31, 32, 33, 34, 35, 36, 37, 38, 39, or 40° C.) (or any temperature in between). In some embodiments, the tissue is placed in the calcium hydroxide solution for about 1-5 days (e.g., about 1, 2, 3, 4, or 5 days, or any time period in between). In some embodiments, the calcium hydroxide solution serves to dissolve undesired tissue components. For example, where the tissue is dermal tissue, the calcium hydroxide solution can dissolve epidermis and enable the manual removal of hair follicles. In certain embodiments, after calcium hydroxide treatment, the calcium hydroxide can be neutralized, for example using acetic acid.

In some embodiments, after decellularization, the tissue sample is washed thoroughly. Any physiologically compatible solutions can be used for washing. Examples of suitable wash solutions include distilled water, phosphate buffered saline (PBS), or any other biocompatible saline solution. In certain embodiments, e.g., when xenogenic or allogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable DNase buffer can be used, as long as the buffer provides for suitable DNase activity.

While an acellular or partially decellularized tissue matrix may be derived from tissue from one or more donor animals of the same species as the intended recipient animal, this is not necessarily the case. Thus, for example, an acellular tissue matrix may be derived from porcine tissue and implanted in a human patient. Species that can serve as donors and/or recipients of acellular tissue matrices include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

In certain embodiments, decellularized tissue can be treated with one or more enzymes to remove undesirable antigens, e.g., an antigen not normally expressed by the recipient animal and thus likely to lead to an immune response and/or rejection of the implanted flowable tissue matrix composition. For example, in certain embodiments, decellularized tissue can be treated with alpha-galactosidase to remove alpha-galactose (α-gal) moieties. In some embodiments, to enzymatically remove α-gal epitopes, after washing tissue thoroughly with saline, the tissue may be subjected to one or more enzymatic treatments to remove α-gal antigens, if present in the sample. In certain embodiments, the tissue may be treated with an α-galactosidase enzyme to eliminate α-gal epitopes. In one embodiment, the tissue is treated with α-galactosidase at a concentration of 0.2 U/ml prepared in 100 mM phosphate buffered saline at pH 6.0. In other embodiments, the concentration of α-galactosidase is reduced to 0.1 U/ml or increased to 0.3, 0.4, or 0.5 U/ml (or any value in between). In other embodiments, any suitable enzyme concentration and buffer can be used, as long as sufficient antigen removal is achieved. In addition, certain exemplary methods of processing tissues to reduce or remove alpha-1,3-galactose moieties are described in Xu et al., *Tissue Engineering*, Vol. 15, 1-13 (2009), which is hereby incorporated by reference in its entirety.

In certain embodiments, animals that have been genetically modified to lack one or more antigenic epitopes may be selected as the tissue source for a flowable tissue matrix composition. For example, animals (e.g., pigs) that have been genetically engineered to lack the terminal α-galactose moiety can be selected as the tissue source. For descriptions of appropriate animals and methods of producing transgenic animals for xenotransplantation, see U.S. patent application Ser. No. 10/896,594 and U.S. Pat. No. 6,166,288, which are hereby incorporated by reference in their entirety.

In some embodiments, the decellularized tissue can be treated to reduce bioburden (i.e., to reduce the number of microorganisms growing on the tissue). In some embodiments, the tissue is treated such that it lacks substantially all bioburden (i.e., the tissue is aseptic or sterile). Suitable bioburden reduction methods are known to one of skill in the art, and may include exposing the tissue to radiation. Irradiation may reduce or substantially eliminate bioburden. In some embodiments, an absorbed dose of 15-17 kGy of e-beam radiation is delivered in order to reduce or substantially eliminate bioburden. In various embodiments, a flowable tissue matrix composition is exposed to between about 5 Gy and 50 kGy of radiation. Suitable forms of radiation can include gamma radiation, e-beam radiation, and X-ray radiation. Other irradiation methods are described in U.S. Application 2010/0272782, the disclosure of which is hereby incorporated by reference in its entirety.

In certain embodiments, after decellularization, viable cells may optionally be seeded in the extracellular matrix. In some embodiments, viable cells may be added to the matrix by standard in vitro cell co-culturing techniques prior to transplantation, or by in vivo repopulation following transplantation. In vivo repopulation can be by the migration of native cells from surrounding tissue into the matrix or by infusing or injecting viable cells obtained from the recipient or from another donor into the matrix in situ. Various cell types can be used, including stem cells such as embryonic stem cells and/or adult stem cells (e.g. mesenchymal stem cells). Any other viable cells can also be used. In some embodiments, the cells are mammalian cells. In certain embodiments, the cells are histocompatible with the subject in which they are implanted. Such cells can promote native tissue migration, proliferation, and/or vascularization. In various embodiments, the cells can be directly applied to the matrix of a decellularized tissue just before or after implantation.

In certain embodiments, one or more additional agents can be added to the extracellular matrix of a decellularized tissue. In some embodiments, the additional agent can comprise an anti-inflammatory agent, an analgesic, or any other desired therapeutic or beneficial agent. In certain embodiments, the additional agent can comprise at least one added growth or signaling factor (e.g., a cell growth factor, an angiogenic factor, a differentiation factor, a cytokine, a hormone, and/or a chemokine). In some embodiments, these additional agents can promote native tissue migration, proliferation, and/or vascularization within the extracellular matrix. In some embodiments, the growth or signaling factor is encoded by a nucleic acid sequence contained within an expression vector. Preferably, the expression vector is in one or more of the viable cells that can be included, optionally, in the extracellular matrix of the decellularized tissue. As used herein, the term "expression vector" refers to any nucleic acid construct that is capable of being taken up by a cell, contains a nucleic acid sequence encoding a desired protein, and contains the other necessary nucleic acid sequences (e.g. promoters, enhancers, termination codon, etc.) to ensure at least minimal expression of the desired protein by the cell.

In various embodiments, the decellularized tissue can be processed into small pieces. In some embodiments, the small pieces are selected to have dimensions that minimize their surface area to volume ratio (e.g., a surface area to volume ratio of less than or equal to about 6 $mm^2/mm^3$). For example, the decellularized tissue can be cut, e.g., using a scalpel or razor, to form small cubes. In some embodiments, the small pieces can have three dimensions (a length, a width, and a height) that each range in size from about 1.0 mm to about 5.0 mm (e.g., about 1.0 mm, 1.5 mm, 2.0 mm, 2.5 mm, 3.0 mm, 3.5 mm, 4.0 mm, 4.5 mm, or 5.0 mm, or any size in between). In some embodiments, the pieces can have regular shapes (e.g., spheres, cubes, rhomboids) or irregular shapes, as long as they generally have dimensions ranging from about 1.0 mm-5.0 mm.

In various embodiments, partially or completely decellularized tissue is gelatinized. In some embodiments, the decellularized tissue is first suspended in an aqueous solution containing a Lewis base, such as sodium carbonate, sodium citrate, and/or sodium acetate. In some embodiments, the Lewis base is present in the solution at a concentration of about 10-30 mM (e.g., about 10, 11, 12, 13, 14, 15, 16, 17, 18, 19, 20, 21, 22, 23, 24, 25, 26, 27, 28, 29, or 30 mM, or any concentration in between). In certain embodiments, the decellularized tissue is present in the aqueous solution at about 0.1-10.0% w/v (dry tissue mass/total solution volume), e.g., about 0.1, 0.2, 0.3, 0.4, 0.5, 1.0, 1.5, 2.0, 3.0, 4.0, 5.0, 6.0, 7.0, 8.0, 9.0, or 10.0% w/v (or any percentage in between). In various embodiments, the decellularized tissue is incubated in the basic solution, with or without agitation, at a temperature of about 40-75° C. (e.g., about 40, 45, 50, 55, 60, 65, 70, or 75° C., or any temperature in between) for about 10-48 hours (e.g., about 10, 15, 20, 24, 36, or 48 hours, or any time period in between). In some embodiments, after incubation, the Lewis base in the suspension is neutralized, for example using HCl at a concentration of about 0.05-0.5 M (e.g., about 0.05, 0.1, 0.15, 0.2, 0.25, 0.3, 0.35, 0.4, 0.45, or 0.5 M, or any concentration in between). In various embodiments, the decellularized tissue suspension is homogenized to form a gelatin. In some embodiments, decellularized tissue is homogenized before incubation in the basic solution, while in other embodiments it is homogenized during or after incubation.

In some embodiments, the gelatinized tissue can be suspended in a hydrating solution. Suitable hydrating solutions include distilled water, phosphate buffered saline (PBS), or any other biocompatible saline solution. In some embodiments, the biocompatible saline solution is at a concentration of about 0.1-10% saline (e.g., about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0, or 10.0%, or any percentage in between). In certain embodiments, the saline suspension is heated to about 40-60° C. (e.g., about 40, 41, 42, 43, 44, 45, 46, 47, 48, 49, 50, 51, 52, 53, 54, 55, 56, 57, 58, 59, or 60° C., or any temperature in between) and then allowed to cool to room temperature, forming a viscous gelatin gel.

In various embodiments, a gelatin gel can be prepared by selecting a biocompatible synthetic gel material having a viscous consistency, such as a hydrogel, starch gel, or other polysaccharide gel. In some embodiments, a gelatin gel is prepared by combining one or more gelatinized tissues with one or more synthetic gel materials.

In certain embodiments, the decellularized tissue or synthetic material in the gelatin gel is present at about 0.1-10.0% w/v (dry mass/total solution volume), e.g., about 0.1, 0.2, 0.3, 0.4, 0.5, 0.6, 0.7, 0.8, 0.9, 1.0, 1.5, 2.0, 3.0, 4.0, 5.0, 6.0, 7.0, 8.0, 9.0, or 10.0% w/v (or any percentage in between).

In some embodiments, a cross-linked gelatin gel can be prepared by adding a cross-linking agent (such as glutaraldehyde, genipin, and/or the reversible cross-linking agent 1, 2, 3, 4, 6-pentagalloyl glucose (PGG)) at a concentration of about 0.01-2.0% (w/v) (e.g., about 0.01, 0.05, 0.1, 0.15, 0.2, 0.25, 0.3, 0.4, 0.5, 0.6, 0.7, 0.8, 0.9, 1.0, 1.5, or 2.0%, or any percentage in between). In certain embodiments, the cross-linking reaction is allowed to proceed at approximately room temperature (e.g., about 19, 20, 21, 22, 23, 24, 25, 26, 27, or 28° C., or any temperature in between) for 12-60 hours (e.g., 12, 15, 20, 24, 36, 48, or 60 hours, or any time period in between). In certain embodiments, the cross-linked gelatin gel is at a concentration of about 0.1-10.0% w/v (dry mass/total solution volume), e.g., about 0.1, 0.2, 0.3, 0.4, 0.5, 0.6, 0.7, 0.8, 0.9, 1.0, 1.5, 2.0, 3.0, 4.0, 5.0, 6.0, 7.0, 8.0, 9.0, or 10.0% w/v (or any percentage in between).

In various embodiments, an implanted flowable tissue matrix composition is prepared such that it has increased resistance to degradation, migration, and/or resorption following implantation into a host tissue, as compared to an implanted homogenized acellular tissue. In certain embodiments, the size of the pieces or fragments of acellular tissue within a flowable composition is a physical parameter affecting the rheological properties, and is also a factor for regulating the biological response upon implantation, for example the ability to resist degradation, migration, and/or resorption. In this regard, in certain embodiments, changes in the surface area to volume ratio of the pieces of decellularized tissue in the flowable composition can alter the kinetics of degradation and remodeling.

Accordingly, in various embodiments, the surface area to volume ratio for a majority of the pieces of decellularized tissue in a flowable tissue matrix composition is minimized (e.g., by reducing the ratio below about 6 mm$^2$/mm$^3$), such that the composition containing these small pieces exhibits moldable rheological properties while increasing resistance to resorption, migration, and/or degradation (e.g., collagenase degradation) following implantation. In some embodiments, the optimized small pieces of decellularized tissue can be combined with gelatinized tissue or gelatin gel. In certain embodiments, the volume of gelatinized tissue or gelatin gel is minimized. In some embodiments, a "minimal volume" of gelatinized tissue or gelatin gel is the amount sufficient to fill the space between the small pieces of decellularized tissue and to allow for an effective flowable composition. For example, about 10-40 g (e.g., about 10, 11, 12, 13, 14, 15, 16, 17, 18, 19, 20, 25, 26, 27, 28, 29, 30, 31, 32, 33, 34, 35, or 40 g, or any amount in between) of decellularized tissue pieces having dimensions of about 1.0-5.0 mm (e.g., about 1.0, 1.5, 2.0, 2.5, 3.0, 3.5, 4.0, 4.5, or 5.0 mm, or any value in between) can be combined with every 1-15 ml of gelatinized tissue or gelatin gel (e.g., about 1, 2, 3, 4, 5, 6, 7, 8, 9, 10, 11, 12, 13, 14, or 15 ml, or any value in between). For example, about 30 g of decellularized tissue having dimensions of about 3.5 mm can be combined with about 9 ml of about 1% gelatin gel to form a flowable tissue matrix composition. In another example, about 15 g of decellularized tissue having dimensions of about 2.2 mm can be combined with about 5 ml of about 1% gelatin gel to form a flowable tissue matrix composition.

In certain embodiments, a flowable tissue matrix composition can comprise, by volume, about 70 to 80% pieces of acellular tissue (e.g., about 70, 72, 74, 76, 78, or 80% or any percentage in between), while the remaining approximately 20 to 30% of the composition (e.g., about 20, 22, 24, 26, 28 or 30% or any percentage in between) can comprise gelatinized tissue or gelatin gel. In some embodiments, a flowable tissue matrix composition can comprise, by mass, about 90 to 98% pieces of acellular tissue (e.g., about 90, 92, 94, 96, or 98% or any percentage in between), while the remaining approximately 2 to 8% of the composition (e.g., about 2, 4, 6, or 8% or any percentage in between) can comprise gelatinized tissue or gelatin gel. In some embodiments, the surface area to volume ratio of the small pieces of decellularized tissue in a flowable tissue matrix composition is less than about 6 mm$^2$/mm$^3$ (e.g., less than about 6.0, 5.0, 4.0, 3.0, 2.0, 1.0, 0.5, 0.4, 0.3, 0.2, or 0.1 mm$^2$/mm$^3$) (or any value in between).

Methods of Use

Disclosed herein are methods of using the flowable tissue matrix compositions described above.

In various embodiments, the flowable tissue matrix compositions can be implanted into a host tissue in need of repair, regeneration, treatment, and/or enhancement. The extracellular matrix provided by the partially or completely decellularized tissue in the compositions provides a scaffold into which native cells from surrounding tissue can migrate and proliferate. Accordingly, in certain embodiments, the extracellular scaffold in a flowable tissue matrix composition can enhance and/or promote tissue treatment, repair, and/or regeneration. Furthermore, as discussed in more detail below, flowable tissue matrix compositions can be used, in certain embodiments, to mold to the shape of an implant site while resisting degradation and/or resorption.

It is known that small particles of acellular tissue (e.g., those having dimensions of less than about 25 microns) are prone to migrate away from an implant site and are more susceptible to degradation following implantation. Furthermore, small particles of acellular tissue are not easily stored in the hydrated state, due to hydrolytic activity and natural phase separation. Thus, such particles are often stored dehydrated, thereby requiring lengthy rehydration and the possibility of over-rehydration prior to surgical use.

Accordingly, in various embodiments, the flowable tissue matrix compositions disclosed herein can overcome the problems associated with the storage and use of small particulate acellular tissue by providing an implantable material that can be stored in hydrated form and which provides increased resistance to degradation and/or resorption following implantation into a host tissue, as compared to an implanted homogenized acellular tissue comprising small particles of less than 25 microns in size, while preserving the desirable moldable properties of particulate tissue. In some embodiments, the surface area to volume ratio of the small pieces of decellularized tissue in a flowable tissue matrix composition is minimized (e.g., by reducing the ratio below about 6 mm$^2$/mm$^3$), for example by using small pieces of decellularized tissue having dimensions of between about 1.0 mm and 5.0 mm. In some embodiments, these small pieces of decellularized tissue are suspended in a minimal amount of gelatinized tissue or gelatin gel (e.g., an amount that minimally fills the spaces between the pieces of tissue), such that the flowable tissue matrix composition retains its moldable properties while increasing its resistance to resorption, migration, and/or degradation (e.g. collagenase degradation) following implantation. In some embodiments, a flowable tissue matrix composition has increased resistance to collagenase degradation, which can be measured, for example, by determining whether at least about 20% (e.g., at least about 20, 30, 40, 50, 60, 70, 80, 90, 95, or 99%, or any percentage in between) of the composition remains after 48 hours of in vitro exposure to about 5 units/mL of Type I collagenase, or after 48 hours of in vivo exposure to an implant site. In certain embodiments, an implanted flowable tissue matrix composition can conform to the contours of an implant site, thereby completely filling the implant site and/or molding to provide support for a desired structure or shape for the implant.

In various embodiments, an implanted flowable tissue matrix composition provides a biocompatible scaffold that supports the native tissue migration, proliferation, and/or revascularization necessary for tissue regeneration, repair, healing, and/or treatment, and does not elicit a substantial immune response that prevents such activity. As used herein, a "substantial immune response" is one that prevents partial or complete tissue regeneration, repair, healing, and/or treatment. In certain embodiments, an implanted flowable tissue matrix composition lacks certain undesirable antigens in order to avoid inducing an immune response. For example, in some embodiments, an implanted flowable tissue matrix composition lacks substantially all α-gal moieties that are known to elicit reactions in humans.

In certain embodiments, the flowable tissue matrix compositions that are implanted in a patient comprise human and/or animal tissue that is completely or substantially free of all cells normally present in the tissue from which the flowable tissue matrix composition is derived. As used herein, "substantially free of all cells" means that the flowable tissue matrix composition contains less than 20%, 10%, 5%, 1%, 0.1%, 0.01%, 0.001%, or 0.0001% (or any percentage in between) of the cells that normally grow within the acellular matrix of the tissue prior to decellularization.

In some embodiments, the implanted flowable tissue matrix compositions can include an extracellular scaffold that has been repopulated with viable cells. Various cell types can be used for repopulation, including stem cells such as embryonic stem cells, adult stem cells (e.g. mesenchymal stem cells), and/or neuronal cells. Any other viable cells can also be used. In some embodiments, the cells are mammalian cells. Such cells can promote native tissue migration, proliferation, and/or revascularization. In various embodiments, the viable cells are applied to the extracellular scaffold of a flowable tissue matrix composition before or after implantation.

In certain embodiments, an implanted flowable tissue matrix composition further comprises one or more additional agents. In some embodiments, the additional agent can comprise an anti-inflammatory agent, an analgesic, or any other desired therapeutic or beneficial agent that promotes tissue repair, regeneration, and/or treatment following implantation. In certain embodiments, the additional agent can comprise, e.g., at least one added growth or signaling factor (e.g., a cell growth factor, an angiogenic factor, a differentiation factor, a cytokine, a hormone, and/or a chemokine). These additional agents can promote native tissue migration, proliferation, and/or vascularization.

Flowable tissue matrix compositions can be implanted in a patient as part of any medical procedure in which tissue repair, regeneration, or treatment is desired. For example, flowable tissue matrix compositions can be implanted following the creation of space between tissue planes as a result of disease, trauma, or surgical intervention. In some embodiments, the composition can be implanted into a space between separated tissue planes and molded to fill the anatomical shape of the implant site. In various embodiments, the implanted composition can provide a scaffold for native tissue migration, proliferation, and revascularization. In certain embodiments, the gelatinized tissue or gelatin gel in a flowable tissue matrix composition can also be used to help reduce or prevent bleeding at the site of implantation.

In another example, flowable tissue matrix compositions can be used as tissue fillers by implanting them following the removal of bulk soft tissue from a patient, e.g., tumor removal. It has been shown that after tumor removal, tissue re-growth is generally poor, especially as to the subcutaneous tissue layers. Generally, a layer of skin will regrow after tumor removal, but the underlying tissue remains unregenerated. Thus, in various embodiments, flowable tissue matrix compositions can be used as implants to replace bulk soft tissue after tumor removal. In certain embodiments, such implants serve as tissue fillers that can be molded to the shape of the implant site while resisting degradation, migration, and/or resorption. In certain embodiments, where the bulk tissue that is removed is near or includes the skin, implantation of a flowable tissue matrix composition can provide the implant site with a more natural look and/or feel after tumor removal. In various embodiments, the implanted composition can also provide a scaffold for native tissue migration, proliferation, and/or revascularization.

In yet another example, flowable tissue matrix compositions can be used for aesthetic purposes, e.g., as implants or in conjunction with traditional implants. For example, flowable tissue matrix compositions can be used to support traditional breast implants, e.g., for use in breast augmentation and/or reconstruction. For example, a flowable tissue matrix composition can be placed around a breast implant and used to fill the space between the implant and surrounding native tissue, thereby providing a smoother contour and/or more natural look and feel for the implant. At the same time, in certain embodiments, the implanted flowable tissue matrix composition can provide a scaffold into which cells from native tissue surrounding the breast implant can grow and proliferate, thereby more firmly securing the breast implant in place and/or reducing the amount of undesirable fibrosis that develops around the implant. In other embodiments, a flowable tissue matrix composition can be used independently as an implant, for example as a collagen implant to increase tissue volume (e.g., lip injections).

EXAMPLES

The following examples serve to illustrate, and in no way limit, the present disclosure.

Example 1: Preparation of Acellular Porcine Dermal Extracellular Matrices

Raw porcine hides were obtained from an abattoir. To prevent the denaturation of the dermal extracellular matrix, the hides were chilled in a refrigerator at 2° C. to 10° C. Subcutaneous fat was mechanically removed from the hides, and skin material was briefly soaked and cleaned in 0.5% (w/v) Triton X-100 solution. Cleaned skin was 3 to 4 mm thick and was trimmed to smaller pieces of about ~8 cm×10 cm.

Skin pieces were then soaked with agitation at room temperature (22° C. to 25° C.) for two days in 0.2% (w/v) calcium hydroxide. The solution to tissue ratio was 500 mL of solution per 100 g of tissue. Epidermis was dissolved during soaking, and after a 30 minute rinse with distilled water, hairs were plucked. After soaking dermal sheets with agitation in 0.2% (w/v) calcium hydroxide for another 3 days, hair follicles were pressed out. Calcium hydroxide treated dermal sheets were washed with distilled water twice, and neutralized with acetic acid to a pH of 7.5. Calcium residue was rinsed off with agitation in distilled water for 8 hours.

Then, dermal sheets were soaked with agitation in a 2.0% (w/v) sodium deoxycholate (SDC) solution dissolved in 10 mM HEPES (4-(2-hydroxyethyl)-1-piperazineethanesulfonic acid) buffer (pH 8.0) containing 10 mM EDTA (ethylenediaminetetraacetic acid). After SDC treatment at 37° C. for 40 hours, dermal sheets were washed in Dulbecco's phosphate buffered saline (PBS) containing 5 mM EDTA (pH 7.3) overnight (~18 hours). The wash solution was changed three times during this washing step. Processed dermal sheets were cut into small cubes at sizes ranging from 1 mm to 5 mm (see FIG. 1 for some examples of such cubes).

Example 2: Preparation of Gelatinized Acellular Porcine Dermis

Figure 2:
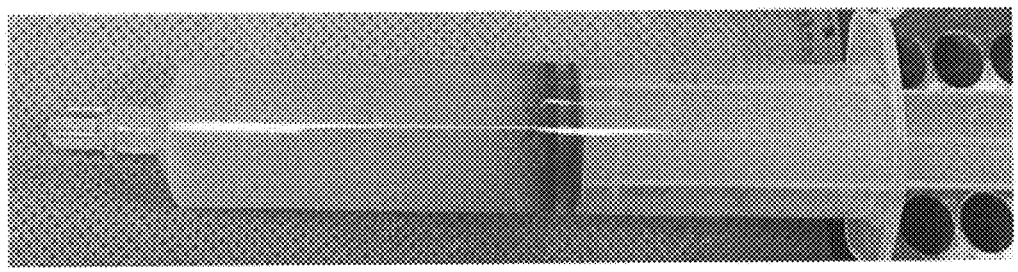
FIG. 2 shows gelatinized acellular porcine dermis (4.0% w/v).

Cubes of porcine dermal acellular tissue (dECM) were suspended in a 20 mM sodium carbonate solution (sterile-filtrated) at 100-mL solution per 4 g dry dECM mass and incubated with agitation at 55° C. to 65° C. over night (~18 hours). The gelatinized tissue suspension was neutralized with 0.1 M HCl before being homogenized into a dECM gel (FIG. 2). Alternatively, dECM cubes were homogenized first in sodium carbonate solution before incubation at 55° C. to 65° C.

Example 3: Preparation of a Purified Gelatin Gel

Figure 3:
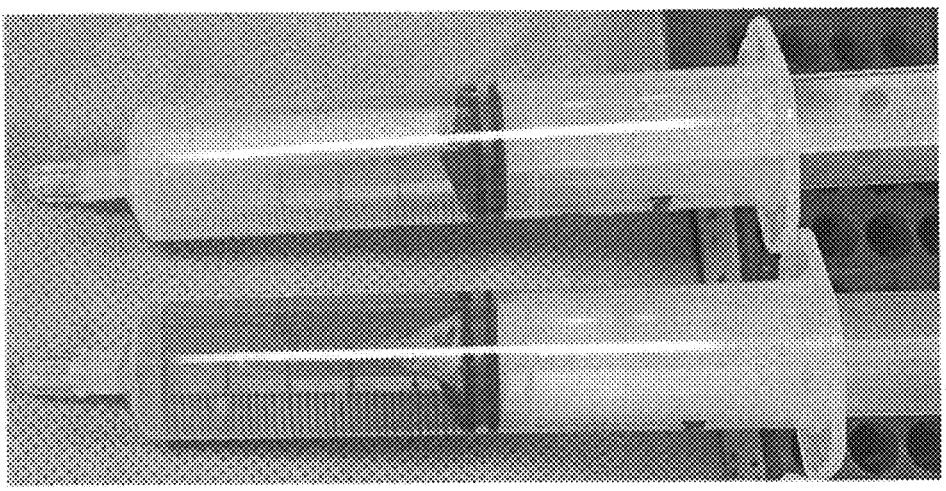
FIG. 3 shows a gelatin gel comprising acellular porcine dermis (1.0% w/v, top syringe) and a cross-linked gelatin gel comprising acellular porcine dermis (0.5%, bottom syringe).

Purified porcine skin gelatin (Sigma-Aldrich, St. Louis, Miss.) was dissolved in 0.9% saline at 50° C. Upon cooling to room temperature, the gelatin suspension became a highly viscous gel (FIG. 3). A cross-linked version of gelatin gel was made with a reversible cross-linker, PGG (1,2,3,4,6-pentagalloyl glucose). An equal volume of 1.0% gelatin gel and 0.1% (w/v) PGG solution was mixed. The cross-linking reaction proceeded at room temperature (22° C. to 25° C.) for 48 hours.

Example 4: Preparation of a Flowable dECM Composition

Figure 4:
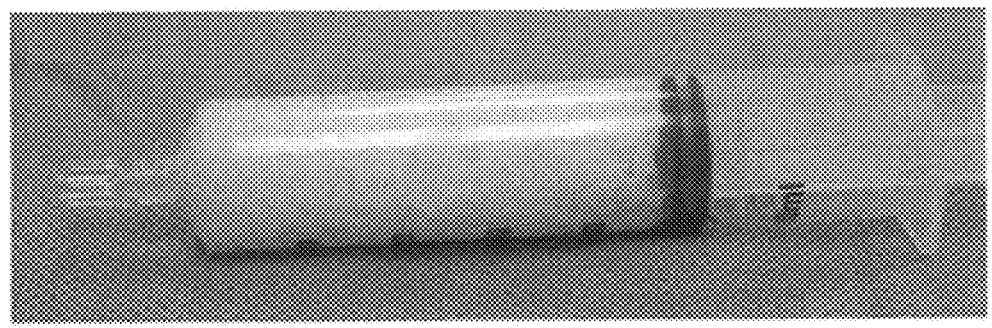
FIG. 4 shows a flowable tissue matrix composition comprising 30 g of cubes of acellular porcine dermis (cube size 3.5 mm+/−0.2 mm) suspended in 9 ml of a 1.0% gelatin gel comprising acellular porcine dermis.

Flowable dECM compositions were prepared by mixing dECM cubes (described in example 1) with gelatinzed dECM (described in example 2) or gelatin gel (described in example 3). The gel volume was kept to the minimum required to fill the void space between dECM cubes and to achieve a stable flowable composition. FIG. 4 shows a stable flowable composition prepared with 30 g of porcine dECM cubes (3.5±0.2 mm) in 9 mL of a 1.0% gelatin gel. A similar composition was made with 15 g of smaller dECM cubes (2.2±0.1 mm) in 5 mL of a 1.0% gelatin gel.

Example 5: Measurement of the Surface Area to Volume Ratio

Figure 5:
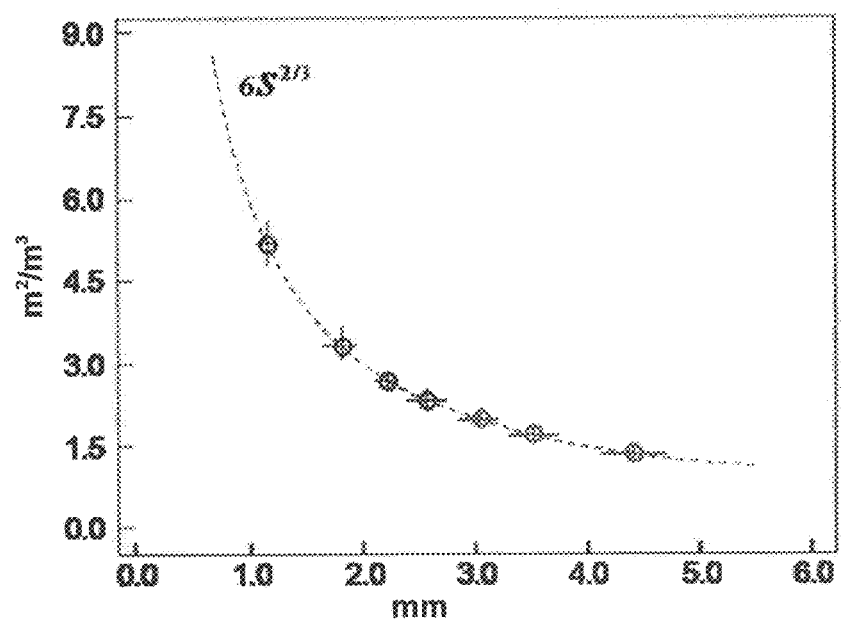
FIG. 5 shows the relationship between cube size (measured in mm) and the surface area to volume ratio (measured in mm$^2$/mm$^3$) for seven cubes that could be used in flowable tissue matrix compositions, and which were produced as described in example 1. The horizontal and vertical bars on each data point indicate standard deviation.

To calculate the volume of a dECM cube, its mass was weighed, and the dECM cube's volume was calculated using its specific density, which was measured at 1.06 g/cm$^3$ by the displacement method. The surface area of the dECM cube was calculated from the dimensions of its faces. FIG. 5 shows the surface area to volume relationship for seven dECM cubes of different sizes. The surface area to volume ratio increases rapidly when the dECM cube has dimensions below 1.0 mm.

Example 6: Resistance to Collagenase Degradation

Figure 6A:
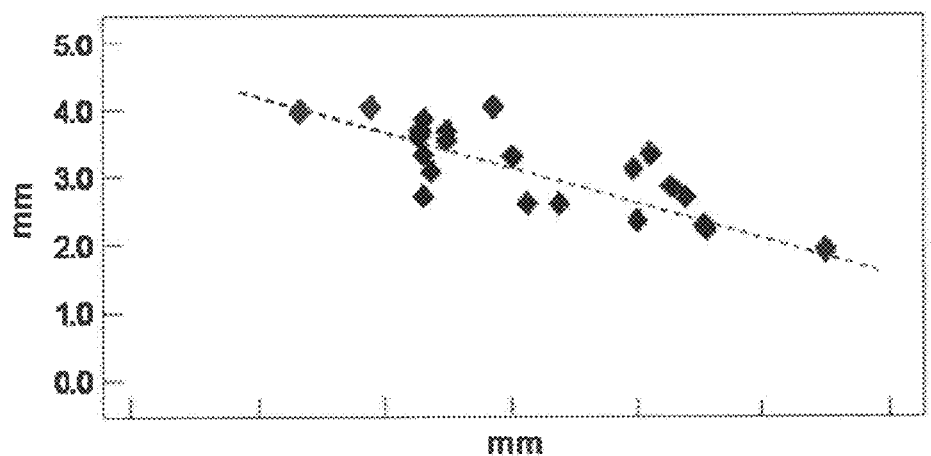
FIG. 6A-B shows the effect of cube size on the resistance to collagenase degradation for the flowable tissue matrix compositions produced according to examples 1-4.
Figure 6B:
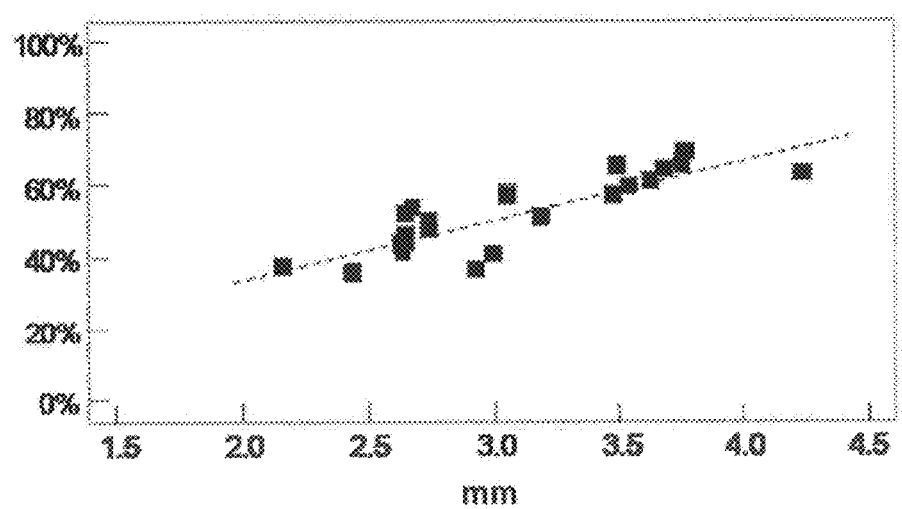

The resistance of dECM cubes of different sizes to collagenase degradation was tested in vitro using type I collagenase. Samples of dECM cubes (697 mg±52 mg) were placed into 30 mL of 10 mM Tris-HCl buffer (pH 7.5) containing 2 mM calcium chloride. Type I collagenase was added to a final activity of 5 units/ml, and samples were incubated with gentle agitation at 37° C. The increase in free amine content in the degradation solution was determined after 18 hours incubation and the amount of tissue remaining was recorded after 48 hours incubation. After 18 hours, a 20-µL aliquot of degradation solution was mixed with 500 µL of 100 mM sodium bicarbonate solution containing 0.05% picryl sulfonic acid (PSA), and reacted at 37° C. for 2 hours. Then 300 µL of 2 M HCl and 2.4 mL of distilled water were added into each sample. The increase in free amine concentration due to protein degradation was determined spectrophotometrically (345 nm) using glycine as a standard. FIG. 6A-B show the effect of dECM cube size on the resistance to collagenase degradation. As dECM cube size decreased, the susceptibility to collagenase degradation increased.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A flowable tissue matrix composition, comprising small pieces of partially or completely decellularized tissue, wherein a majority of the small pieces of partially or completely decellularized tissue have surface area to volume ratio of less than about 6 mm$^2$/mm$^3$ and wherein the small pieces of partially or completely decellularized tissue are suspended in a gelatin gel comprising less than about 20% of the composition on a volume/volume (v/v) basis.

2. The composition of claim 1, wherein the small pieces of partially or completely decellularized tissue in the composition have an increased resistance to degradation or resorption as measured using a type I collagenase digestion assay, as compared to a homogenized acellular tissue, while also retaining the ability to flow into and mold to the shape of an implant site.

3. The composition of claim 1, wherein the small pieces of partially or completely decellularized tissue have a length, a width, and a height ranging from about 1.0 mm to about 5.0 mm.

4. The composition of claim 3, wherein the length, width, and height of the majority of the small pieces of partially or completely decellularized tissue ranges from about 2.0 mm to 4.0 mm.

5. The composition of claim 1, wherein the majority of the small pieces of partially or completely decellularized tissue in the composition have a surface area to volume ratio of greater than about 1.5 mm$^2$/mm$^3$ and less than about 6 mm$^2$/mm$^3$.

6. The composition of claim 1, wherein the majority of the small pieces of partially or completely decellularized tissue in the composition have a surface area to volume ratio of less than about 4.5 mm$^2$/mm$^3$ and greater than about 2.0 mm$^2$/mm$^3$.

7. The composition of claim 1, wherein the gelatin gel is crosslinked.

8. The composition of claim 1, wherein the small pieces of partially or completely decellularized tissue are derived from an animal selected from a group consisting of human, nonhuman primate, pig, cow, horse, goat, sheep, dog, cat, rabbit, guinea pig, gerbil, hamster, rat, and mouse.

9. The composition of claim 1, wherein the small pieces of partially or completely decellularized tissue are derived from a tissue selected from a group consisting of bone, skin, dermis, intestine, vascular, urinary bladder, tendon, ligament, muscle, fascia, neurologic tissue, vessel, liver, heart, lung, kidney, and cartilage tissue.

10. The composition of claim 1, wherein the flowable tissue matrix composition lacks alpha-galactose moieties.

11. The composition of claim 1, further comprising one or more viable cells.

12. The composition of claim 11, wherein the one or more viable cells are mammalian cells.

13. The composition of claim 11, wherein the one or more viable cells are stem cells.

14. The composition of claim 1, further comprising at least one additional factor selected from a group consisting of an anti-inflammatory agent, an analgesic, a cell growth factor, an angiogenic factor, a differentiation factor, a cytokine, a hormone, and a chemokine.

15. The composition of claim 14, wherein the at least one additional factor is encoded by a nucleic acid sequence contained within an expression vector.

16. The composition of claim 15, wherein the expression vector is contained within one or more viable cells.

17. The composition of claim 1, wherein the flowable tissue matrix composition has been subjected to a sterilization process.

18. The composition of claim 1, wherein the gelatin gel comprises a gelatinized tissue that has been heated to at least about 50° C. and then allowed to cool.

19. The composition of claim 18, wherein the gelatinized tissue comprises homogenized acellular or partially decellularized tissue in an aqueous solution at a concentration of about 0.1-10.0% weight/volume (w/v).

20. The composition of claim 1, wherein the gelatin gel comprises at least one of a hydrogel or a starch gel.

* * * * *